(12) United States Patent
Blattner et al.

(10) Patent No.: US 7,935,505 B2
(45) Date of Patent: May 3, 2011

(54) PLASMID DNA PREPARATIONS AND METHODS FOR PRODUCING SAME

(75) Inventors: Frederick R. Blattner, Madison, WI (US); John Walter Campbell, Oak Park, IL (US); Guy Plunkett, Madison, WI (US)

(73) Assignee: Scarab Genomics, LLC, Madison, WI (US)

( * ) Notice: Subject to any disclaimer, the term of this patent is extended or adjusted under 35 U.S.C. 154(b) by 0 days.

(21) Appl. No.: 12/294,159

(22) PCT Filed: May 24, 2007

(86) PCT No.: PCT/US2007/069685
§ 371 (c)(1),
(2), (4) Date: Sep. 23, 2008

(87) PCT Pub. No.: WO2007/140274
PCT Pub. Date: Dec. 6, 2007

(65) Prior Publication Data
US 2009/0068707 A1      Mar. 12, 2009

(51) Int. Cl.
*C12N 15/64*          (2006.01)
(52) U.S. Cl. ............... 435/91.4; 435/320.1; 435/252.33
(58) Field of Classification Search .................. None
See application file for complete search history.

(56) References Cited

U.S. PATENT DOCUMENTS

| | | |
|---|---|---|
| 5,997,881 A | 12/1999 | Powell et al. |
| 6,080,849 A | 6/2000 | Bermudes et al. |
| 6,548,287 B1 | 4/2003 | Powell et al. |
| 6,750,333 B1 | 6/2004 | Kuhne |

OTHER PUBLICATIONS

International Search Report of PCT/US07/069685 dated Nov. 7, 2007.
Karow, M., et al., "Isolation and Characterization of the *Escherichia coli* msbB Gene, A Multicopy Suppressor of Null Mutations in the High-Temperature Requirement Gene htrB," Journal of Bacteriology, vol. 174, No. 3, pp. 702-710 (1992).
Meier-Dieter, U., et al., "Biosynthesis of Enterobacterial Common Antigen in *Escherichia coli*," vol. 265, No. 23, pp. 13490-13497 (1990).
Samuel, G., et al., "Biosynthesis of O-Antigens: Genes and Pathways Involved in Nucleotide Sugar Precursor Synthesis and O-Antigen Assembly," Carbohydrate Research, vol. 338, pp. 2503-2519 (2003).
Vorachek-Warren, M., et al., "A Triple Mutant of *Escherichia coli* Lacking Secondary Acyl Chains on Lipid A*," The Journal of Biological Chemistry, vol. 277, No. 16, pp. 14194-14205 (2002).
Wang, L., et al., "Organization of *Escherichia coli* O157 O Antigen Gene Cluster and Identification of Its Specific Genes," Infection and Immunity, vol. 66, No. 8, pp. 3545-3551 (1998).

*Primary Examiner* — James S Ketter
(74) *Attorney, Agent, or Firm* — Morgan Lewis & Bockius LLP

(57) ABSTRACT

The various embodiments of the present invention relate generally to plasmid DNA preparations and to methods for producing and using such preparations.

10 Claims, No Drawings

PLASMID DNA PREPARATIONS AND METHODS FOR PRODUCING SAME

CROSS REFERENCE TO RELATED APPLICATIONS

This application is the National Stage of International Application Number PCT/US2007/069685, filed May 24, 2007, which claims the benefit of U.S. Provisional Patent Application No. 60/808,500, filed May 24, 2006, which is incorporated herein by reference.

FIELD OF THE INVENTION

The various embodiments of the present invention relate generally to plasmid DNA preparations and to methods for producing and using them.

BACKGROUND OF THE INVENTION

Plasmid DNAs are potential therapeutic agents for many human and animal diseases. Many of these plasmid DNAs are too large to produce by chemical synthesis and therefore are most efficiently produced by propagating them in a host cell, which is in turn grown on a nutrient medium to high density. The DNA is subsequently recovered from the host cells. Isolation and purification of plasmid DNA from complex mixtures involves multiple stages of purification. The first stage includes concentrating the cells from fermentation media, which is composed of unconsumed nutrients as well as cellular waste products. The next stage requires lysis or disruption of the cells, which results in a complex biochemical mixture of cellular constituents including the plasmid DNA of interest. This is typically done in the presence of chaotropic salts to minimize enzymatic activity, which can degrade plasmid DNA, or can be accomplished by mechanical means such as with a pressure cell, sonicator, hydrodynamic shearing device, or bead beater in conjunction with an enzyme inhibitor to minimize DNA degradation. The next stage of plasmid preparation involves physically separating soluble plasmid DNA from insoluble material such as membranes, denatured proteins and large chromosomal DNA fragments by centrifugation, differential precipitation or filtration. This produces a cleared lysate containing plasmid DNA, which can be further purified by direct precipitation, phase partitioning or by adsorption to various resins via ion exchange or hydrophobic interaction methods and combinations thereof, which may be followed by precipitation or phase partitioning of plasmid DNA. Chromatographic purification can be accomplished by batch or column chromatographic methods and may involve indirect, via compatible ion, or direct adsorption methods. All these methods are well known to those skilled in the art and each step is designed to remove impurities and contaminants from plasmid DNA. All purification regimens can be improved by reducing the amount and complexity of the material from which the plasmid DNA is isolated. This includes potential contaminants in the media as well as material produced by the host cell.

One significant impurity present in cellular preparations derived from bacterial cells is endotoxin, which is in part derived from lipopolysaccharide (LPS) present in the outer membrane of bacteria. Gram-negative bacteria such as E. coli require at least a minimal structural component of LPS for viability and wholesale deletion of genes that encode the pathways required for biosynthesis of these structures is lethal. However, a few genes involved in LPS synthesis are not essential, and the cell can tolerate deletion or loss of function of these specific genes. Many attempts have been made to manipulate such genes to improve the endotoxin profile of bacteria without demonstrable success. One notable exception is the discovery that deletion of msbB, which encodes myristoyl acyltransferase, produces a cell with a 1000-10,000-fold reduction in the ability to stimulate TNFα by human tissue culture cells (Sommerville et al., J. Clin. Invest. 1996 97:359). The use of msbB mutants to produce LPS deficient cells capable of producing DNA with lowered endotoxin levels and use of such cells as tumor targeted vectors is disclosed in a number of U.S. patents (e.g., U.S. Pat. Nos. 6,548,287; 6,080,849; and 5,997,881).

The chromosome of E. coli contains many cryptic prophage and insertion sequence (IS) elements that represent horizontally transferred genes that have moved into E. coli over time. Removal of these horizontally transferred sequences and other non-essential genes produces multiple deletion strain (MDS) variants such as that described by Blattner and co-workers (Posfai et al., Science 2006 312:1044; U.S. Pat. No. 6,989,265 and in PCT/US03/01800, published as WO 03/070880, all of which are incorporated herein by reference in their entirety). These cells are unique in that they lack significant numbers of genes relative to other E. coli strains commonly used in production of plasmid DNA. However, these strains remain completely prototrophic and are capable of robust growth on defined minimal media. Defined minimal media for E. coli typically includes the following (g/l): 5 g glucose, 6 g $Na_2HPO_4$, 3 g $KH_2PO_4$, 1 g $NH_4Cl$, 0.5 g NaCl. 0.12 g $MgSO_4$ and 0.01 g $CaCl_2$.

Plasmid DNA preparations from cells grown in defined minimal media will lack many of the undefined components entrained from the undefined components of rich media necessary for efficient growth of auxotrophic bacterial cell lines commonly used to produce plasmid DNA. The use of defined minimal media, with a limited number of chemically known nutrient sources, for growth of plasmid containing bacterial cells will result in lowering the number of media derived contaminants, as well as provide a more uniform cellular composition from which plasmid DNA must be subsequently purified. In addition, the lack of uncontrolled lysis during fermentation of MDS strains due to removal of all cryptic prophage lysis functions, as well as the reduced biochemical complexity of MDS cells due to removal of many genes from the chromosome, also reduces the number of proteins and other biological components within the lysate. Indeed, plasmid DNA produced from MDS strains which remain completely proficient for LPS production and retain all genes known to affect LPS synthesis, have significantly reduced levels of endotoxin by LAL assay relative to other commonly used bacterial cell lines, even when grown in rich undefined media.

Production of plasmid DNAs for use as human therapeutics requires minimizing the amount of bacterial endotoxin remaining in the purified DNA product. Biological production of plasmid DNAs in bacterial hosts provides an efficient and scalable method for producing large quantities of plasmids. However, purification of plasmid DNA from bacterial hosts, by any combination of methods currently practiced does not completely eliminate endotoxin from the prepared DNA. If plasmid DNA could be produced having lower levels of endotoxin than available by current methods, a significant advance in the art would result.

SUMMARY OF THE INVENTION

In one embodiment, the present invention provides plasmid DNA preparations. In another embodiment, the plasmid DNA comprises reduced endotoxin levels. Methods for producing and using such plasmid DNA preparations are also provided. In one embodiment, the plasmid DNA is prepared by a method comprising the steps of a) growing plasmid DNA in a multiple deletion strain bacteria; b) lysing the multiple deletion strain bacteria to produce a lysate; c) isolating at least a portion of the plasmid DNA from the lysate; and purifying the isolated plasmid DNA. Multiple deletion strain bacteria lacking genes involved in production of lipoplysaccharide and/or enteric common antigen are also provided.

These and other embodiments of the present invention are described in more detail herein below.

DETAILED DESCRIPTION OF THE INVENTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the pertinent art at issue. Also, the disclosure of ranges is intended as a continuous range including every value between the minimum and maximum values recited as well as any ranges that can be formed by such values. This includes ranges that can be formed that do or do not include a finite upper and/or lower boundary. This also includes ratios that are derivable by dividing a given disclosed numeral into another disclosed numeral. Accordingly, the skilled person will appreciate that many such ratios, ranges, and ranges of ratios can be unambiguously derived from the data and numbers presented herein and all represent various embodiments of the present invention.

In various embodiments, the present invention provides methods for producing a plasmid DNA. In one embodiment, the plasmid DNA has reduced endotoxin levels. In another embodiment, the method comprises the steps of a) growing plasmid DNA in a multiple deletion strain bacteria; b) lysing the multiple deletion strain bacteria to produce a lysate; c) isolating at least a portion of the plasmid DNA from the lysate; and purifying the isolated plasmid DNA.

The term "multiple deletion strain (MDS) bacteria" herein means a bacteria having about 1% to about 75% of its protein coding genes deleted, for example about 5%, about 10%, about 20%, about 30% about 40%, about 50% or about 60% of the protein coding genes deleted. In one embodiment, the term "MDS bacteria" refers to bacteria for which removal of the above amounts of protein coding region does not unacceptably affect the ability of the organism to grow on minimal medium. Whether removal of two or more genes "unacceptably affects" the ability of the organism to grow on minimal medium in the present context depends on the specific application. For example, a 30% reduction in proliferation rate may be acceptable for one application but not another. In addition, adverse effect of deleting a DNA sequence from the genome may be reduced by measures such as changing culture conditions. Such measures may turn an otherwise unacceptable adverse effect to an acceptable one. In one embodiment, the proliferation rate is approximately the same as the parental strain. However, proliferation rates ranging from about 5%, 10%, 15%, 20%, 30%, 40% to about 50% lower than that of the parental strain are within the scope of the invention. More particularly, doubling times of bacteria of the present invention may range from about five minutes to about three hours. Non-limiting examples of suitable MDS bacteria are disclosed in U.S. Pat. No. 6,989,265, and U.S. Pat. Pub. Nos. 20060270043 and 2006/0199257, each of which is hereby incorporated by reference herein.

In one embodiment, suitable MDS bacteria lack genes b0246-b0310, b1336-b1411, b2441-b2450, b2622-b2660, b1994-b2008, b3323-b3338, b2349-b2363, b1539-b1579, b4271-b4320, b2968-b2987, b1137-b1172, b0538-b0565, b0016-b0022, b0577-b0582, b2389-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4325-b4358, b0497-b0502, b0700-b0706, b1456-b1462, b3482-b3484, b3593-b3596, b0981-b0988, b1021-b1031, b2080-b2096, b3441-b3446, b3557-b3558 of the *E. coli* strain K12 MG1655.

Various bacterial strains can be used in embodiments of the present invention including, without limitation, *E. coli, Salmonella* and other gram negative bacterium.

Various protein coding genes can be deleted to form MDS bacteria. In *E. coli* and other bacteria, as well as in higher organisms, a type of DNA sequence that can be deleted includes those that in general will adversely affect the stability of the organism or of the gene products of that organism. Such elements that give rise to instability include without limitation transposable elements, insertion sequences, and other "selfish DNA" elements which may play a role in genome instability. For example, insertion sequence (IS) elements and their associated transposes are often found in bacterial genomes, and thus are targets for deletion. IS sequences are common in *E. coli*, and all of them may be deleted. For purposes of clarity in this document, we use the term IS element and transposable element generically to refer to DNA elements, whether intact or defective, that can move from one point to another in the genome. An example of the detrimental effects of IS elements in science and technology is the fact that they can hop from the genome of the host *E. coli* into a BAC plasmid during propagation for sequencing. This artifact could be prevented by deletion from the host cells of all IS elements. For a specific application, other specific genes associated with genomic instability may also be deleted.

In one embodiment, the MDS bacteria lacks a functional msbB gene. In another embodiment, the MDS bacteria lacks one or more genes implicated in or necessary for production of a lipopolysaccharide. The term "lipopolysaccharide" herein refers generally to is a large molecule comprising a lipid and a polysaccharide (carbohydrate) joined by a covalent bond. Lipopolysaccharides typically comprise a core oligosaccharide, Lipid A and polysaccharide (O) side chains.

Genes implicated in and/or necessary for production of a lipopolysaccharide are known in the art, for example as disclosed in Reeves P, Wang L (2002). Genomic organization of LPS-specific loci. *Curr Top Microbiol Immunol* 264 (1): 109-35 and Patil P et al., (2004). Variation suggestive of horizontal gene transfer at a lipopolysaccharide (lps) biosynthetic locus in *Xanthomonas oryzae* pv. *oryzae*, the bacterial leaf blight pathogen of rice. *BMC Microbiol* 4 (1): 40, each of which are hereby incorporated by reference herein. In one embodiment, candidate genes for deletion include msbB, as well as other LPS biosynthetic genes occurring in the rfa gene cluster between nucleotide 3792010 and 3806121 of the *E. coli* chromosome. Additional illustrative genes implicated in or necessary for production of lipopolysaccharide include rfaI, rfaJ, rfe genes (required for the biosynthesis of O side chains of the lipopolysaccharide).

Additional deletions to further reduce endotoxin levels may also include the genes associated with production of the enteric common antigen (ECA), a repeating trisaccharide carbohydrate moiety that occurs in multiple forms including in association with immunogenic glycolipids and as cyclic multimers either of which may constitute a variant form of endotoxin. The ECA genes are generally clustered on the *E. coli* chromosome between nucleotide 3965939 and 3980295.

In one embodiment, plasmid DNA prepared according to methods of the invention have reduced enotoxin levels by comparison with an otherwise similar comparative plasmid DNA grown in bacteria of the same bacteria as the multiple deletion strain bacteria, but wherein the comparative bacteria does not contain multiple deletions. In various embodiments, plasmid DNA prepared according to methods of the invention comprise an approximate 1% to about 95% reduction in endotoxin, for example at least a 75%, at least a 60%, at least a 50%, at least a 40%, at least a 30%, at least a 20%, at least a 20%, at least a 5% or at least a 2.5% reduction by comparison with an otherwise similar plasmid DNA grown in bacteria of the same strain as the multiple deletion strain bacteria, but that does not contain multiple deletions.

While the exact chemical nature of endotoxin is imprecise, the designation is generally understood to include a range of molecules which are typically composed of sugars, fatty acids and various other substituents. Endotoxin is frequently quantified using FDA approved methods based on various assays involving the *limulus* amoebocyte lysate (LAL), which is derived from Horseshoe Crab blood products and are well known to those skilled in the art. The *limulus* amoebocyte lysate method is described in New England Journal of Medicine, Vol. 289, No. 18, 931-934 (1973) and U.S. Pat. No. 4,107,007, each of which is hereby incorporated by reference herein. *Limulus* amoebocyte lysate is an aqueous extract of blood cells (amoebocytes) from the horseshoe crab, *Limulus polyphemus*. The endotoxins activate an enzyme in the *Limulus* amoebocyte lysate which then reacts with low molecular weight clottable proteins to form a gel. Typically, 0.1 ml solution of a freeze-dried *Limulus* lysate preparation sold commercially under the trademark Pyrotell® is mixed with 0.1 ml of a test sample, then allowed to incubate undisturbed for one hour at 37° C. A positive test is indicated by the formation of a gel which does not collapse upon 180 degree inversion of the test tube. To quantify the amount of endotoxin in body fluid, serial dilution of test samples can be performed to determine the lowest dilution which will give the above-described positive result. Samples can be prepared for detection according to methods disclosed in U.S. Pat. No. 4,276,050, hereby incorporated by reference herein. Endotoxin can also be quantified according to the LAL chromagenic kinetic assay (Endochrome-K™) as is well known in the art.

In another embodiment, the present invention provides plasmid DNA having an endotoxin concentration of less than about 200 EU/mg DNA, less than about 150 EU/mg DNA, less than about 100 EU/mg DNA, less than about 50 EU/mg DNA, less than about 20 EU/mg DNA, less than about 10 EU/mg DNA, less than about 9 EU/mg DNA, less than about 8 EU/mg DNA, less than about 7 EU/mg DNA, less than about 6 EU/mg DNA, less than about 5 EU/mg DNA, less than about 4 EU/mg DNA, less than about 3 EU/mg DNA, less than about 2 EU/mg DNA, less than about 1 EU/mg DNA, less than about 0.5 EU/mg DNA, less than about 0.25 EU/mg DNA, less than about 0.2 EU/mg DNA, less than about 0.15 EU/mg DNA or less than about 0.05 EU/mg DNA prior to any treatment with an endotoxin removal agent. The term "endotoxin removal agent" herein typically refers to a borate-based or borate-containing compound that interacts with sugar moieties associated with endotoxin. Illustrative purification kits and compositions that include an endotoxin removal agent are the Wizard MagneSil TfX™ System by Promega, EndoFree® by Qiagen, and MiraCLEAN® by Mirus. In one embodiment, plasmid DNA is not contacted with an endotoxin removal agent in carrying out the process of producing the above-described low endotoxin plasmid DNA. In another such embodiment, the plasmid DNA is bacterially produced.

Plasmid DNAs according to various embodiments of the present invention have broad application. Such plasmid DNA can illustratively be used as a vaccine for prevention of infectious disease, as cloning vectors to express genes coding for various protein products, etc.

MDS bacteria lacking one or more genes involved in or necessary for production of a lipopolysaccharide or enteric common antigen represent further embodiments of the invention.

EXAMPLES

Example 1

Cells were grown in yeast extract, tryptone based media in 1 liter shake flasks at 37° C. Purified super-coiled plasmid was prepared by low speed centrifugation, cell lysis and removal of insoluble debris using methods well known in the art (see, e.g., Current Protocols in Molecular Biology, Eds. Ausubel et al., John Wiley and Sons, 2001). Plasmid DNA was further purified by ion-exchange chromatography followed by compatible ion separation on hydrophobic resin. The level of endotoxin in the resulting plasmid DNAs was tested by LAL chromagenic kinetic assay (Endochrome-K™, Charles River Laboratories) as shown in Table 1.

TABLE 1

| | Endotoxin assay | | | |
|---|---|---|---|---|
| Sample | Bacterial host strain | Plasmid DNA concentration (mg/ml) | Endotoxin concentration (EU/ml) | Effective endotoxin level (EU/mg DNA) |
| 1 | DH10B | 6.33 | 100 | 15.8 |
| 2 | MDS42 recA | 1.34 | 1.90 | 1.42 |
| 3 | MDS42 | 1.23 | 1.28 | 1.04 |
| 4 | MDS42 recA lacZΔM15 | 1.25 | 0.162 | 0.129 |

As can be seen from Table 1, plasmid DNA prepared from multiple deletion strain bacteria had much lower endotoxin concentrations and effective endotoxin levels compared with strain DH10B.

Example 2

A plasmid containing a gene encoding Green Fluorescence Protein (GFP) transcriptionally coupled to a CMV promoter and a gene encoding resistance to the aminoglycoside G418, was isolated from various bacterial host strains with a commercial plasmid isolation kit that uses a silica gel membrane for the adsorption purification step (QIAprep Spin column, Qiagen, Valencia, Calif.). These plasmid preparations were tested for toxicity in a COS1 monkey kidney cell transfection assay. The assay involves liposome mediated transfection of 4 µg of plasmid DNA added to $2.5 \times 10^4$ COS1 cells followed by 24 hour outgrowth in selective media. The liposome mediated transfection reaction is well known in the art and is described by many sources, e.g., Current Protocols in Molecular Biology, Eds. Ausubel et al., John Wiley and Sons, 2001). Ten randomly selected fields of microscope view were selected from each culture dish and the total number of cells within each field counted. A FITC filter (488 nm cutoff) was used to discriminate cells expressing GFP within each view and the overall transformation efficiency calculated by dividing the number of GFP expressing cells by the total number of cells. Two trials were completed and the results are shown in Table 2.

TABLE 2

Transfection efficiency

| Source of DNA | DH5α | MG1655 | MG1655 ΔmsbB | MDS42 |
|---|---|---|---|---|
| Trial 1 | 50% | 51% | 59% | 72% |
| Trial 2 | 51% | — | — | 69% |

As can bee seen from Table 2, transformation efficiency was higher in multiple deletion strain bacteria as compared to control strains, including MG1655 having a mutated msbB gene.

Example 3

A further test of endotoxin-associated toxicity was carried out with the same plasmid and tissue culture system described in Example 2. In this case transfection was carried out by adding 4 µg of plasmid DNA in lipofection reagent to $1.0 \times 10^5$ COS1 cells, followed by 24 hour outgrowth in non-selective media. The cultures were stained with 0.3% trypan blue dye and washed three times with sterile phosphate buffered saline to remove dead cells. Ten randomly selected fields of microscope view were selected from each culture dish and the total number of cells within each field counted. Two trials were conducted with results shown in Table 3.

TABLE 3

Number of live COS1 cells post-transfection

| Source of DNA | no DNA | DH5α | MDS42 | MDS42 msbB |
|---|---|---|---|---|
| Trial 1 | 288 | 226 | 259 | 284 |
| Trial 2 | 330 | 221 | 230 | 288 |

Deletion of LPS associated genes may lower endotoxin levels in plasmid DNAs recovered from such strains even further.

As shown in the examples, methods of the invention provide plasmid DNA isolated form bacterial strains lacking the ECA genes. This plasmid DNA has very low endotoxin and therefore can be transfected into tissue culture cells with higher efficiency and less cytotoxicity than plasmid DNA isolated from bacterial culture of cells that retain the ECA gene cluster. The cytotoxicty appears to be most effectively reduced when the ECA gene cluster deletion is coupled with an msbB mutation. Use of the ECA, msbB deletion strain for plasmid production, when the plasmids are to be used for subsequent transfection into tissue culture cells, allows the researcher to work with standard plasmid recovery kits rather than the more expensive endotoxin reducing kits (such as those marketed by Promega, Invitrogen and Qiagen) since the ECA, msbB strains have inherently reduced the endotoxin in recovered DNA by genetic means.

What is claimed is:

1. An *E. coli* multiple deletion strain which lacks:
   (a) a functional msbB gene; and
   (b) one or more genes involved in production of enteric common antigen, selected from the genes located on the *E. coli* strain K12 MG1655 chromosome between nucleotide 3965939 and 3980295.

2. A method for producing a plasmid DNA with reduced endotoxin levels, comprising:
   (a) growing said plasmid DNA in the multiple deletion strain bacteria of claim 1;
   (b) lysing said multiple deletion strain bacteria to produce a lysate;
   (c) isolating said plasmid DNA from said lysate to form isolated plasmid DNA; and
   (d) purifying the isolated plasmid DNA.

3. The method of claim 2 where said multiple deletion strain is prototrophic in minimal media.

4. The method of claim 2 wherein the plasmid DNA contains less than 200 EU/mg DNA of endotoxin prior to purification of the plasmid DNA with an endotoxin removal agent.

5. The method of claim 2 wherein the plasmid DNA contains less than 50 EU/mg DNA of endotoxin prior to purification of the plasmid DNA with an endotoxin removal agent.

6. The method of claim 2 wherein the plasmid DNA contains less than 0.1 EU/mg DNA of endotoxin prior to purification of the plasmid DNA with an endotoxin removal agent.

7. The multiple deletion strain of claim 1, said multiple deletion strain having deleted therefrom all genes located on the *E. coli* strain K12 MG1655 chromosome between nucleotide 3965939 and 3980295.

8. The multiple deletion of strain of claim 1, said multiple deletion strain having deleted therefrom one or more genes selected from the genes located on the *E. coli* strain K12 MG1655 chromosome between nucleotide 3792010 and 3806121.

9. The multiple deletion strain of claim 7, wherein said multiple deletion strain has a genome that is smaller than 4.00 Mb.

10. The multiple deletion strain of claim 9, wherein said multiple deletion strain lacks genes b0246-b0310, b1336-b1411, b2441-b2450, b2622-b2660, b1994-b2008, b3323-b3338, b2349-b2363, b1539-b1579, b4271-b4320, b2968-b2987, b1137-b1172, b0538-b0565, b0016-b0022, b0577-b0582, b2389-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4325-b4358, b0497-b0502, b0700-b0706, b1456-b1462, b3482-b3484, b3593-b3596, b0981-b0988, b1021-b1031, b2080-b2096, b3441-b3446, b3557-b3558 of the *E. coli* strain K12 MG1655.

* * * * *